United States Patent [19]  [11] Patent Number: 4,519,944
Dahill et al.  [45] Date of Patent: May 28, 1985

[54] SPIROLACTONES AS ODORANTS

[75] Inventors: Robert T. Dahill, Holmdel; Kenneth L. Purzycki, Lake Parsippany; Erlinda F. Golle, Passaic, all of N.J.

[73] Assignee: Givaudan Corporation, Clifton, N.J.

[21] Appl. No.: 495,212

[22] Filed: May 16, 1983

Related U.S. Application Data

[63] Continuation-in-part of Ser. No. 411,145, Aug. 25, 1982, abandoned.

[51] Int. Cl.$^3$ ..................... A61K 7/46; C07D 307/94
[52] U.S. Cl. ................... 252/522 R; 549/265
[58] Field of Search ..................... 252/522 R; 549/265

[56] References Cited

U.S. PATENT DOCUMENTS 2,839,538  6/1958  Nemec ................... 549/265

FOREIGN PATENT DOCUMENTS 105157  4/1984  European Pat. Off. ............ 549/265

OTHER PUBLICATIONS

Derwent Abstract of J51095058.
Derwent Abstract of J77042794.
Derwent Abstract of J55076843.
Walling et al., "Organic Reactions", vol. 13, (1963) pp. 114 & 136.
Arctander, "Perfume and Flavor Chemicals", II, (1975) 2350.
Jacobson et al., "Jou. Org. Chem.", vol. 45 (1980) pp. 395–405.
Moulines et al., "C.A.", vol. 64, 3607a.
Moulines et al., "Bull. Soc. Chim. France", (1971) pp. 1075–1080.
Nikishin et al., "C.A.", vol. 58, 7826c.

*Primary Examiner*—Anton H. Sutto
*Attorney, Agent, or Firm*—Robert F. Tavares

[57] ABSTRACT

Fragrance compositions comprising 8-alkyl-1-oxaspiro[4.5]decan-2-ones wherein the alkyl group contains from one to four carbon atoms.

27 Claims, No Drawings

SPIROLACTONES AS ODORANTS

RELATED U.S. APPLICATION DATA

This is a continuation-in-part of Serial No.: 06/411,145 filed August 25, 1982, now abandoned.

SUMMARY OF THE INVENTION

This invention relates to fragrance compositions comprising 8-alkyl-1-oxaspiro[4.5]decan-2-ones of the formula

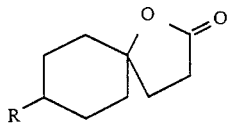

wherein R represents an alkyl group of from one to four carbon atoms. Formula I is intended to represent the possible stereoisomers and mixtures thereof.

Each of the compounds represented by formula I makes a unique and individual contribution to a fragrance formulation. While it has been found that the cis- and trans-isomers of each of the compounds of formula I differ in their odor properties, the odors of the isomers complement one another and, as a result, it is preferred to use such isomeric mixtures. Compounds represented by formula I have been found useful in a variety of fragrance formulations including bases of the woody, floral, fruity, oriental, and resinous types.

The spirolactones of this invention may be prepared by a number of methods, many of which are similar to methods described in the literature for preparing lactones. See, for example methods described in U.S. Pat. No. 2,839,538; J. Moulines and R. Lalande, Compte. Rend. 261, 1983 (1965); J. Moulines and R. Lalande, Bull. Soc. Chim. France, 1075–80 (1971); G. I. Nikishin and V. D. Vorob'ev, Isvestiya Akademii Nauk SSSR, Otdelenie Khimicheskikh Nauk No. 10 (1962) 1874–1876; and C. Walling and E. S. Huyser, Org. Reactions 13, 114 (1963).

Cis- and trans- spirolactones, as defined herein, refer to those compounds where the alkyl group R and the oxygen bonded to the cyclohexyl ring are either cis or trans to one another.

DESCRIPTION OF THE PREFERRED EMBODIMENTS

The preferred method for the preparation of the spirolactones of this invention involves reacting acrylic acid or an ester of acrylic acid with an excess (5 to 10 equivalents) of the appropriate cyclohexanol in the presence of a catalytic amount of a free radical initiator such as di-t-butylperoxide (about 0.05 to 0.5 equivalents) at a temperature sufficient to initiate the reaction, about 145°–155° C. being preferred in the case of di-t-butylperoxide. This method provides an isomeric mixture which corresponds to the isomeric mixture of the starting alcohols. While the cis- and trans-isomers have somewhat different odors and can be separated by techniques known in the art such as column chromatography, preparative gas chromatography and the like, it is far more economical to use the isomeric mixtures as produced in the reaction. Fortuitously, the odors of the isomers are complementary and the isomeric mixtures are preferred over the individual components for most fragrance compositions.

Table I provides odor descriptions for a number of the spirolactones of formula I which were prepared according to the method described above.

TABLE I

| R | Odor Description |
|---|---|
| CH$_3$ | strong, creamy, lactone, coumarin, slightly cresylic |
| C$_2$H$_5$ | intense, creamy, lactone, slightly woody |
| iso-C$_3$H$_7$ | woody, milky-lactone, dry-powdery |
| sec-C$_4$H$_9$ | peach, apricot, lactone |
| tert-C$_4$H$_9$ | woody, amber, weak |

The compounds wherein R is isopropyl or ethyl, i.e. 8-isopropyl-1-oxaspiro[4.5]decan-2-one and 8-ethyl-1-oxaspiro [4.5]decan-2-one, are especially preferred for use in fragrance compositions. Both are intense and of good tenacity, the ethyl analog being of much greater intensity. While these compounds are perceptibly different from one another, they are complementary and can often be used together to good advantage. For example, a small amount of the ethyl compound can be added to the isopropyl compound to enhance the creamy notes where such enhanced creaminess is desirable.

The compound wherein R is isopropyl can be prepared from commercially available p-isopropylcyclohexanol and acrylic acid to provide a product which is from about 35% to 55% of the cis-isomer and 45% to 65% of the trans-isomer, usually 40%–50% cis and 50%–60% trans. The odor of this product is described as woody, milky-lactone, dry (powdery), intense, and of good tenacity. Because of these woody, milky-lactone notes, this compound is especially preferred for use in a number of rich, full bodied compositions of the precious-woody type such as sandalwood and vetiver or in woody, dry, resinous compositions such as moss. In addition to these, the 8-isopropyl-1-oxaspiro[4.5]decan-2-one is also especially useful in oriental blends, floral bouquets, and the like.

The compound wherein R is ethyl provides a similar ratio of isomers when prepared from p-ethylcyclohexanol, i.e. usually 40% to 50% of the cis-isomer and 50% to 60% of the trans-isomer. The odor of this product is described as intense, creamy lactone, slightly woody. The ethyl analog is described as having a stronger creamy character than the isopropyl analog and to be especially useful in fragrance formulations where this rich, creamy-lactone quality is desirable, especially in florals such as Gardenia, Jasmin and Tuberose and precious-woody compositions such as sandalwood. Because of the intensity and character of its odor, the 8-ethyl-1-oxaspiro[4.5]decan-2-one may be used, usually in small quantities, for imparting fullness and richness to a wide variety of odorant bases.

In formulations wherein it is desirable to add a rich, creamy, woody complex, it is found beneficial to use a mixture of the 8-ethyl-1-oxaspiro[4.5]decan-2-one and the 8-isopropyl-1-oxaspiro[4.5]decan-2-one. The ethyl analog blends well with the isopropyl analog and adds to and enhances the creamy notes. Only small amounts of the ethyl derivative are required to enhance the creamy notes of the isopropyl derivative, the ethyl derivative having an odor intensity many times that of the isopropyl derivative. It is preferred to use about 0.05% to 1.0% of the ethyl derivative in such mixtures, with about 0.1% to 0.5% being especially preferred. The presence of the ethyl derivative at these levels enhances the creamy contribution and is most beneficial in formulations of the precious-woody type such as sandalwood wherein a rich, creamy, woody complex odor is highly desirable in achieving a natural sandalwood odor. Of course, higher ratios could be used where it is desirable to accentuate the creamy notes with respect to the woody notes of the isopropyl derivative.

The compounds wherein R is methyl or secondary-butyl are also highly preferred for use in fragrance compositions. For the compound wherein R is methyl, i.e. 8-methyl-1-oxaspiro-[4.5]decan-2-one, the isomer ratio is about 40% cis and 60% trans. This product has its own unique odor. It is described as having creamy-lactone odor properties reminiscent of the ethyl derivative, but is also described as being reminiscent of coumarin, slightly cresylic and not as fruity as the ethyl analog. The methyl analog is also several times less intense than the 8-ethyl-1-oxaspiro[4.5]decan-2-one. Because of its basic creamy-lactone character, it is also useful in a wide variety of odorant formulations in which a creamy-lactone quality is desirable. In addition, its coumarin notes make it particularly useful in formulating coumarin type specialties and in fragrance formulations wherein coumarin-like notes are desirable.

The novel compound wherein R is sec-butyl, i.e. 8-sec-butyl-1-oxaspiro[4.5]decan-2-one, is similarly prepared from p-sec-butylcyclohexanol and acrylic acid to form an isomeric mixture of about 30% to 45% cis and about 55% to 70% trans, usually 33% to 43% cis and 57% to 67% trans. The odor of these mixtures is described as fruity in the direction of peach and apricot. This sec-butyl analog is particularly useful for imparting these natural fruity notes to fragrance compositions. These notes are most desirable in floral bouquests such as White Rose, Jasmin, Narcissus, etc. in which they make a contribution to the natural character of the fragrance. In addition to these, the 8-sec-butyl-1-oxaspiro[4.5]decan-2-one is useful in a wide variety of fragrance compositions not only to contribute odor characteristics but to blend and enhance other notes present in the composition. For example, in fragrance bases of the precious-woody type such as sandalwood and vetiver, the sec-butyl analog can be used to soften and modify the precious wood odors. In fine fragrances such as the chypre type, it adds a fruity odor which blends and modifies the woody, moss and citrus notes.

A number of desirable effects that can be achieved by the use of a compound of formula I in fragrance compositions are demonstrated by the accompanying examples wherein the compounds were incorporated in bases of the vetiver, sandalwood, moss, amber, and White Rose types.

Sandalwood, vetiver and moss compositions were described as better blended, fuller and richer after the addition of a compound of formula I. Individual effects were additionally noted for each compound. In the sandalwood and vetiver bases the 8-isopropyl-1-oxaspiro[4.5]decan-2-one, at levels of 10% and 20% respectively, reenforced and enhanced the precious-woody character inherent in these bases while adding a soft creaminess. In the moss composition the presence of 15% of the isopropylspirolactone added to and rounded out the dominant woody character. The 8-ethyl-1-oxaspiro[4.5]decan-2-one used at 0.6% and 1.2% respectively added a sweet creaminess to the sandalwood and vetiver bases. The fragrances of the bases were described as being more intense especially that of the vetiver. The vetiver base was also used to demonstrate the coumarin quality of the 8-methyl-1-oxaspiro[4.5]decan-2-one. When 4% of coumarin was removed from the vetiver and 23% of the methylspirolactone was added not only was a full, rich, lactone quality added but some of the sweet hay-like contribution of coumarin was returned.

Amber and White Rose compositions demonstrate the ability of compounds of formula I to add nuances to bases when used in relatively small amounts. An amber composition was found to be creamier and better balanced after the addition of a compound of formula I. Here, when used at 1% the creamy notes of the methylspirolactone added lift and body, while the creamy, woody notes of the isopropyl analog provided a softer and more sophisticated fragrance. This base and the White Rose base were used to demonstrate the odor strength of the ethylspirolactone as especially small amounts of this compound were found to have impact on both bases. The amber base was made richer and creamier by 0.05% of the ethyl analog while 0.03% added to the White Rose base enhanced its natural quality by adding a desirable fatty character.

The White Rose base was generally found to be better blended and more natural after the addition of a compound of formula I. The isopropyl analog at 0.5% had an effect somewhat similar to that of the ethyl, i.e. enhanced the natural floral character of the composition making it more reminiscent of a natural rose oil. The 8-sec-butyl-1-oxaspiro[4.5]decan-2-one, also at 0.5%, blended and enhanced the fruity character of the base by imparting a natural peach note providing a more finished and natural floral fragrance.

The compounds of formula I may be used in a range of about 0.01% to 30% in odorant compositions. The practical range of 0.01% to 5% is preferred for the very intense ethyl analog while the practical range of 0.5% to 30% is preferred for the other analogs.

The use and concentration in a fragrance base would of course depend on the desired effect and be limited only by the perfumer's skill in the art. The higher concentrations of 5% and 30% as recommended above should not be construed as limiting since a creative perfumer may have need for higher concentrations in certain cases, especially to create special effects.

Odorant compositions containing compounds of formula I may be used as odorant bases for the preparation of perfumes and toilet waters by adding the usual alcoholic and aqueous diluents thereto. Approximately 15-20% by weight of base would be used for perfumes and approximately 2-5% by weight would be used for toilet waters.

Similarly, the base compositions can be used to odorize soaps, detergents, cosmetics, or the like. In these instances, a base concentration of from about 0.5% to about 2% by weight can be used.

ILLUSTRATION OF THE PREFERRED EMBODIMENTS

The following examples are intended to illustrate embodiments of this invention as it is now preferred to practice it. It should be understood that such examples are merely illustrative and the invention is to be limited only as indicated in the claims. Perfume ingredients are given in parts by weight in grams. When the material used is better known by its common name, tradename or trademark such a name is used with the chemical name being given in parentheses. Analysis of reaction products was conducted on a Perkin Elmer 900 gas chromatograph using either a 1/16 in.×500 ft, 2% Carbowax 20M column or a ⅛ in.×20 ft. 2% OV-101 column.

The odor of the individual isomers was determined by smelling the isomer as it eluted from the exit port of the gas chromatograph.

EXAMPLE I

Preparation of oxaspiro[4.5]decan-2-ones (I)

I-a. 8-Isopropyl-1-oxaspiro[4.5]decan-2-one

To 1247 g of 4-isopropylcyclohexanol at 143°–150° C. was added in 6 hrs a mixture of 71.1 g (1.0 m) acrylic acid, 142 g (1.0 m) 4-isopropylcyclohexanol and 14.6 g (0.1 m) di-tert-butylperoxide. After an additional hour at 143°–150° the mixture was distilled at reduced pressure yielding 142.1 g. Bp:125°–141° C. (1.0 mm Hg). Odor:woody, milky-lactone, dry. Analysis:99% pure by VPC: 44% cis (odor:nonalactone, celery-lactone) 56% trans (odor:strong woody, cinnamic, urine)

Similarly prepared were:

I-b. 8-Methyl-1-oxaspiro[4.5]decan-2-one

Bp:97°–100° C. (0.5 mm Hg). Odor:strong, creamy, lactone, coumarin, slightly cresylic. Analysis:99+% pure by VPC; 40% cis (odor:rich, woody, lactone) 60% trans (odor:urinaceous, milky lactone, slight cresylic)

I-c. 8-Ethyl-1-oxaspiro[4.5]decan-2-one

Bp:121°–130° C. (0.5 mm Hg). Odor:Intense, creamy, lactone slightly woody. Analysis:99% pure by VPC; 42% cis (odor:creamy, peachy lactone) 58% trans (odor: slight cinnamic aldehyde, creamy lactone)

I-d. 8-sec-Butyl-1-oxaspiro[4.5]decan-2-one

Bp:164°–180° C. (0.5 mm Hg). Odor:peach, apricot lactone. Analysis:99% pure by VPC; 37% cis (odor:nonalactone, celery-lactone) 63% trans (odor:weak leathery urine)

I-e. 8-tert-Butyl-1-oxaspiro[4.5]decan-2-one

Bp:140°–142° C. (0.5 mm Hg). Odor:woody, amber. Analysis:99% pure by VPC; 32% cis (odor:lactone-peachy, nonalactone) 68% trans (odor:urine, woody-lactone)

EXAMPLE II

Use of formula I compounds in fragrance compositions

| A. Vetiver Base | |
|---|---|
| Components | Parts |
| Vetiver oil Bourbon | 290 |
| Santalol | 200 |
| Hydroxycitronellal | 90 |
| Cinnamic Alcohol | 50 |
| Heliotropin | 60 |
| Coumarin | 30 |
| Musk Ketone (4-t-butyl-3,5-dinitro-2,6-dimethylacetophenone) | 50 |
| Musk Ambrette (6-t-butyl-3-methyl-2,4-dinitroanisole) | 30 |
| | 800 |

The vetiver base as formulated above was perceived to be unblended. The Vetiver oil and the other ingredients did not blend well and the composition was described as having chemical notes.

The addition of 9.96 parts (1.2%) of 8-ethyl-1-oxaspiro[4.5]decan-2-one blended these notes by adding a sweetness and creaminess. The vetiver base with the ethyl compound added was described as being more intense and more natural.

The addition of 200 parts (20%) of 8-isopropyl-1-oxaspiro[4.5]decan-2-one also blended the discordant notes while enhancing the precious-woody character. The base with the compound added was described as being softer and creamier overall, resulting in a more natural vetiver fragrance. If 200 parts of a mixture containing 8-isopropyl-1-oxaspiro[4.5]decan-2-one and from about 0.1% to 0.5% of 8-ethyl-1-oxaspiro[4.5]decan-2-one is used in place of the pure isopropyl derivative the resulting fragrance base is more creamy and is more intense and natural.

To demonstrate the effect of 8-methyl-1-oxaspiro[4.5]-decan-2-one the above base was also formulated without the 30 parts of coumarin. The base without the coumarin was perceived to be thinner, woodier and without the sweet-hay effect of coumarin. The addition of 230 parts (23%) of 8-methyl-1-oxaspiro[4.5]-decan-2-one had a beneficial effect on the base, adding a sweet odor similar to that of coumarin but with more lactone character resulting in a more rounded vetiver fragrance.

| B. Sandalwood Base | |
|---|---|
| Components | Parts |
| Sandalore ® (Givaudan) [3-Methyl-5-(2,2,3-trimethylcyclopent-3-en-1-yl)-pentan-2-ol] | 300 |
| Musk Ambrette (6-t-Butyl-3-methyl-2,4-dinitroanisole) | 50 |
| Amyris Oil | 20 |
| Hydroxycitronellal | 30 |
| Methylionone | 100 |
| Benzyl Benzoate | 400 |
| | 900 |

The sandalwood base as formulated above was somewhat thin i.e. the composition lacks body, fullness.

The addition of 5.0 parts (0.6%) of 8-ethyl-1-oxaspiro[4.5]decan-2-one enhanced the creaminess of the fragrance and gave the base fullness and a more natural sandalwood top note.

The addition of 100 parts (10%) of 8-isopropyl-1-oxaspiro-[4.5]decan-2-one both enhanced the woody character and added a creamy note and fullness that improved the base, resulting in a more desirable sandalwood fragrance. If 100 parts of 8-isopropyl-1-oxaspiro[4.5]decan-2-one containing from about 0.1% to 0.5% of 8-ethyl-1-oxaspiro[4.5]decan-2-one is used the creamy note is even more pronounced, creating a sandalwood fragrance that is even more natural.

| C. Moss Base | |
|---|---|
| Components | Parts |
| Lemon Oil Terpenes | 70 |
| Lime Oil (distilled) | 50 |
| Orange Oil California | 30 |
| Amyl Salicylate Prime | 20 |
| Benzyl Salicylate | 30 |
| Coumarin | 50 |
| Heliotropin | 80 |
| Folione ® (Givaudan) (Methyl 2-octynoate) | 10 |
| 4-Acetyl-6-t-butyl-1,1-dimethyl indan | 40 |
| Oakmoss Soluble Resin | 50 |
| Lilial ® (Givaudan) (p-t-Butyl-α-methylhydrocinnamaldehyde) | 100 |
| Phenyl Ethyl Alcohol | 100 |
| Terpineol-α | 60 |
| Hydroxycitronellal | 40 |

-continued

| C. Moss Base | |
|---|---|
| Components | Parts |
| Diethyl Phthalate | 120 |
| | 850 |

The moss base as formulated above was perceived to have an unblended woody character that dominated the composition. The addition of 150 parts (15%) of 8-isopropyl-1-oxaspiro[4.5]-decan-2-one balanced the moss fragrance by blending the dominant woody note into the base and rounding out the overall woody impression.

| D. Amber Base | |
|---|---|
| Components | Parts |
| Labdanum Resin Soluble | 376.3 |
| Patchouly Moyenne | 19.8 |
| Benzoin Soluble Resin | 99.0 |
| Vetiver Bourbon | 49.5 |
| Sandalwood E.I. | 99.0 |
| Mousse de Chene Absolute (50% in Ethanol) | 19.8 |
| Musk Ambrette (6-t-Butyl-3-methyl-2,4-dinitroanisole) | 49.5 |
| Musk Ketone (4-t-Butyl-3,5-dinitro-2,4-dimethylacetophenone) | 49.5 |
| Vanillin U.S.P. | 49.5 |
| Bergamot Oil N.S. | 69.3 |
| Orange California C.P. | 49.5 |
| Rose 392/2* | 49.5 |
| Castoreum Absolute (10% in Ethanol) | 9.9 |
| | 990.1 |

*(Specialty Base of the Givaudan Corp.)

Notes of a citrusy, animalic and sweet nature were perceived to be somewhat unblended in the amber base as formulated above. The addition of 9.9 parts (1.0%) of 8-methyl-1-oxaspiro[4.5]decan-2-one or of 8-isopropyl-1-oxaspiro[4.5]decan-2-one blended these discordant notes into the composition. The methylspriolactone made the base stronger (i.e. added lift and body), creamier and sweeter. The isoproplyspirolactone added a rich, creamy, slightly-woody character that created a softer, amber fragrance.

The addition of 0.49 parts (0.05%) of 8-ethyl-1-oxaspiro[4.5]decan-2-one to the amber base similarly added a creamy slightly woody character but with a much stronger lactone effect. The labdanum notes were more noticeable.

| E. White Rose Base | |
|---|---|
| Components | Parts |
| Palmarosa oil | 400 |
| Ginger Grass oil | 100 |
| Geranium Algerian | 50 |
| Citronellol | 150 |
| Benzyl Acetate | 100 |
| Phenyl Ethyl Acetate | 60 |
| Phenyl Ethyl Alcohol | 40 |
| Aldehyde Mixture* | 5 |
| Methylionone | 20 |
| α-Ionone | 60 |
| Nonylic Alcohol | 10 |
| | 995 |

*(Equal parts by weight of n-octanal, n-nonanal and n-decanal)

The White Rose base, as formulated above, contained unblended fruity notes. When the base was formulated with 0.25 parts (0.03%) of 8-ethyl-1-oxaspiro[4.5]decan-2-one, or with 5 parts (0.5%) of either 8-isopropyl-1-oxaspiro[4.5]decan-2-one or 8-sec-butyl-1-oxaspiro[4.5]decan-2-one these discordant notes were blended into a uniform composition. The ethylspirolactone and the isopropylspirolactone also enhanced the natural quality of the rose fragrance by adding a desirable fatty or creamy character. The sec-butylspirolactone enhanced the basic fruity character by adding a natural peach note. All the bases were found to be more desirable, finished floral fragrances.

We claim:

1. A method for improving the odor of a fragrance composition which comprises adding thereto a compound of the formula

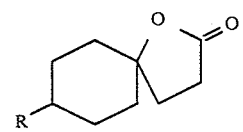

wherein R represents an alkyl group of from one to four carbon atoms.

2. The method of claim 1 wherein the compound to be added is 8-methyl-1-oxaspiro[4.5]decan-2-one.

3. The method of claim 1 wherein the compound to be added is 8-ethyl-1-oxaspiro[4.5]decan-2-one.

4. The method of claim 1 wherein the compound to be added is 8-isopropyl-1-oxaspiro[4.5]decan-2-one.

5. The method of claim 1 wherein the compound to be added is 8-sec-butyl-1-oxaspiro[4.5]decan-2-one.

6. A compound having the formula

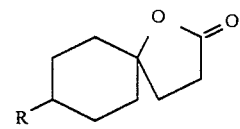

wherein R is selected from the group consisting of methyl, ethyl and sec-butyl.

7. A compound according to claim 6 wherein R is methyl.

8. A compound according to claim 7 which consists essentially of 35% to 45% of the cis-8-methyl-1-oxaspiro[4.5]-decan-2-one and 55% to 65% of the trans-8-methyl-1-oxa-spiro[4.5]decan-2-one.

9. A compound according to claim 6 wherein R is ethyl.

10. A compound according to claim 9 which consists essentially of 40% to 50% of the cis-8-ethyl-1-oxaspiro[4.5]-decan-2-one and 50% to 60% of the trans-8-ethyl-1-oxaspiro-[4.5]decan-2-one.

11. A compound according to claim 6 wherein R is sec-butyl.

12. A compound according to claim 11 which consists essentially of 33% to 43% of the cis-8-sec-butyl-1-oxaspiro[4.5]-decan-2-one and 57% to 67% of the trans-8-sec-butyl-1-oxaspiro[4.5]decan-2-one.

13. A fragrance composition comprising an olfactorily effective amount of a compound of the formula

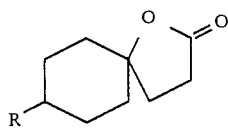

wherein R represents an alkyl group of from one to four carbon atoms, and at least one other olfactory agent.

14. A composition according to claim 13 wherein R is methyl, ethyl, iso-propyl, sec-butyl or tert-butyl.

15. A composition according to claim 14 wherein the compound is 8-methyl-1-oxaspiro[4.5]decan-2-one.

16. A composition according to claim 15 wherein the 8-methyl-1-oxaspiro[4.5]decan-2-one is a mixture consisting of 35%–45% of the cis-isomer and 55%–65% of the trans-isomer.

17. A composition according to claim 14 wherein the compound is 8-ethyl-1-oxaspiro[4.5]decan-2-one.

18. A composition according to claim 17 wherein the 8-ethyl-1-oxaspiro[4.5]decan-2-one is a mixture consisting of 40%–50% of the cis-isomer and 50%–60% of the trans-isomer.

19. A composition according to claim 14 wherein the compound is 8-isopropyl-1-oxaspiro[4.5]decan-2-one.

20. A composition according to claim 19 wherein the 8-isopropyl-11-oxaspiro[4.5]decan-2-one is a mixture consisting of 35–55% of the cis-isomer and 45–65% of the trans-isomer.

21. A composition according to claim 19 wherein the 8-isopropyl-1-oxaspiro[4.5]decan-2-one is a mixture consisting of 40–50% of the cis-isomer and 50–60% of the trans-isomer.

22. A composition according to claim 19 wherein the fragrance is a sandalwood or vetiver type.

23. A composition according to claim 14 wherein the compound is 8-sec-butyl-1-oxaspiro[4.5]decan-2-one.

24. A composition according to claim 23 wherein the 8-sec-butyl-1-oxaspiro[4.5]decan-2-one is a mixture consisting of 30–45% of the cis-isomer and 55–70% of the trans-isomer.

25. A composition according to claim 23 wherein the 8-sec-butyl-1-oxaspiro[4.5]decan-2-one is a mixture consisting of 33–43% of the cis-isomer and 57–67% of the trans-isomer.

26. A composition according to claim 13 wherein the composition comprises an olfactorily effective amount of a mixture consisting essentially of 8-isopropyl-1-oxaspiro[4.5]decan-2-one and 8-ethyl-1-oxaspiro[4.5]decan-2-one.

27. A composition according to claim 26 which is essentially 99% to 99.95% of a 40%–50% cis and 50%–60% trans mixture of 8-isopropyl-1-oxaspiro[4.5]decan-2-one and 0.05% to 1.0% of a 40%–50% cis and 50%–60% trans mixture of 8-ethyl-1-oxaspiro[4.5]decan-2-one.

* * * * *